(12) United States Patent
Li et al.

(10) Patent No.: US 11,090,170 B2
(45) Date of Patent: Aug. 17, 2021

(54) ACETABULAR CUP PROSTHESIS POSITIONING INSTRUMENT AND METHOD

(71) Applicant: ORTHOSOFT INC., Montreal (CA)

(72) Inventors: Di Li, LaSalle (CA); Louis-Philippe Amiot, Montreal (CA); Herbert Andre Jansen, Freiburg (DE); Francois Paradis, Boucherville (CA); Isabelle Robitaille, St-Ignace-de-Loyola (CA); Bruno Falardeau, Verdun (CA); Karine Duval, Montreal (CA); Myriam Valin, Laval (CA); Yvan Leone, Montreal (CA); Yonik Breton, Montreal (CA); Benoit Pelletier, Laval (CA); Mathieu Chevrier, Roxboro (CA); Jerome Casaubon, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 238 days.

(21) Appl. No.: 15/968,868

(22) Filed: May 2, 2018

(65) Prior Publication Data

US 2018/0250144 A1 Sep. 6, 2018

Related U.S. Application Data

(62) Division of application No. 14/301,877, filed on Jun. 11, 2014, now Pat. No. 9,987,148.

(Continued)

(51) Int. Cl.
*A61F 2/46* (2006.01)
*A61B 90/13* (2016.01)
(Continued)

(52) U.S. Cl.
CPC ............ *A61F 2/4609* (2013.01); *A61B 90/13* (2016.02); *A61B 2034/104* (2016.02);
(Continued)

(58) Field of Classification Search
CPC ........... A61F 2/4609; A61F 2002/4623; A61B 90/13; A61B 2034/104; A61B 2034/2048
See application file for complete search history.

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Hofmann et al, "Natural-Knee II System", Intermedics Orthopedics, Austin, TX, 1995.

*Primary Examiner* — Matthew J Lawson
(74) *Attorney, Agent, or Firm* — Norton Rose Fulbright Canada LLP (57) ABSTRACT

A method for assisting in positioning the acetabular cup comprises orienting a cup positioning instrument with a cup thereon in an initial reference orientation relative to an acetabulum of a pelvis with the cup forming a joint with the acetabulum, the cup positioning instrument comprising an inertial sensor unit with pre-planned orientation data for a desired cup orientation based on at least one landmark of the pelvis, The cup positioning instrument is rotated to a desired abduction angle as guided by an interface of the cup positioning instrument, based on movements relative to at least one landmark. The cup positioning instrument is rotated to (Continued)

a desired anteversion angle as guided by the interface of the cup positioning instrument, based on movements relative to the at least one landmark. Upon reaching the desired cup orientation as indicated by the interface, the cup is impacted into the acetabulum.

9 Claims, 5 Drawing Sheets

Related U.S. Application Data (60) Provisional application No. 61/833,654, filed on Jun. 11, 2013.

(51) Int. Cl.
*A61B 34/10* (2016.01)
*A61B 34/20* (2016.01)

(52) U.S. Cl.
CPC ..... *A61B 2034/2048* (2016.02); *A61F 2/4603* (2013.01); *A61F 2002/4687* (2013.01)

(56) References Cited

U.S. PATENT DOCUMENTS

| | | | |
|---|---|---|---|
| 5,490,854 A | 2/1996 | Fisher et al. |
| 5,768,134 A | 6/1998 | Swaelens et al. |
| 5,871,018 A | 2/1999 | Delp et al. |
| 5,916,219 A | 6/1999 | Matsuno et al. |
| 6,991,655 B2 | 1/2006 | Iversen |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,167,823 B2 | 5/2012 | Nycz |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,911,447 B2 * | 12/2014 | van der Walt ....... A61B 17/155 |
| | | | 606/102 |
| 2003/0055502 A1 | 3/2003 | Lang et al. |
| 2003/0153829 A1 | 8/2003 | Sarin |
| 2003/0216669 A1 | 11/2003 | Lang et al. |
| 2004/0092944 A1* | 5/2004 | Penenberg ............ A61F 2/3609 |
| | | | 606/91 |
| 2004/0133276 A1 | 7/2004 | Lang et al. |
| 2004/0138754 A1 | 7/2004 | Lang et al. |
| 2004/0147926 A1 | 7/2004 | Iversen |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0070897 A1* | 3/2005 | Petersen ............... A61B 17/155 |
| | | | 606/53 |
| 2005/0182320 A1 | 8/2005 | Stifter |
| 2005/0203536 A1 | 9/2005 | Laffargue et al. |
| 2005/0209604 A1 | 9/2005 | Penenberg |
| 2005/0234461 A1 | 10/2005 | Burdulis et al. |
| 2005/0267584 A1 | 12/2005 | Burdulis et al. |
| 2006/0064109 A1 | 3/2006 | Iversen |
| 2006/0111722 A1 | 5/2006 | Bouadi |
| 2006/0184177 A1 | 8/2006 | Echeverri |
| 2007/0043375 A1* | 2/2007 | Anissian ................ A61B 17/15 |
| | | | 606/87 |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0051910 A1 | 2/2008 | Kammerzell et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 | 10/2008 | Lang et al. |
| 2008/0269757 A1 | 10/2008 | McMinn |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |

(56) References Cited

U.S. PATENT DOCUMENTS

| | | |
|---|---|---|
| 2009/0099567 A1 | 4/2009 | Zajac |
| 2009/0099665 A1* | 4/2009 | Taylor ................. A61F 2/34 623/22.21 |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarksi et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0137869 A1* | 6/2010 | Borja ................... A61B 17/155 606/88 |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0249657 A1* | 9/2010 | Nycz ................... A61F 2/4609 600/587 |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0152871 A1 | 6/2011 | Park |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0022406 A1 | 1/2012 | Hladio |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0136402 A1 | 5/2012 | Burroughs |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0157887 A1 | 6/2012 | Fanson |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |

(56) References Cited

U.S. PATENT DOCUMENTS

| | | |
|---|---|---|
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2012/0323247 A1 | 12/2012 | Bettenga |
| 2012/0330319 A1 | 12/2012 | Birkbeck |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0046310 A1 | 2/2013 | Ranawat |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0261632 A1 | 10/2013 | Livorsi |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0052149 A1 | 2/2014 | van der Walt |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2014/0094925 A1 | 4/2014 | Satterthwaite |
| 2014/0276871 A1* | 9/2014 | Sherman ............... A61F 2/4609 606/91 |
| 2014/0276889 A1* | 9/2014 | Head ............... A61F 2/4657 606/102 |
| 2014/0303631 A1 | 10/2014 | Thornberry |
| 2015/0305891 A1* | 10/2015 | Bergin ............... A61B 17/1746 606/91 |
| 2015/0313723 A1* | 11/2015 | Jansen ............... A61B 90/11 606/91 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2736525 A1 | 3/2010 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1563810 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |

(56) References Cited

FOREIGN PATENT DOCUMENTS

| | | |
|---|---|---|
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2005-224613 A | 8/2005 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2004/112640 A1 | 12/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010/030809 A1 | 3/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

* cited by examiner

ACETABULAR CUP PROSTHESIS POSITIONING INSTRUMENT AND METHOD

CROSS-REFERENCE TO RELATED APPLICATION

The present application is a divisional application of Ser. No. 14/301,877 filed on Jul. 11, 2014 which claims the priority of U.S. Provisional Application Ser. No. 61/833,654, filed on Jun. 11, 2013 and incorporated herein SPE by reference.

FIELD OF THE APPLICATION

The present application relates to computer-assisted surgery for hip using inertial sensors.

BACKGROUND OF THE ART

During orthopedic implant procedures, e.g. total hip replacement (THR), the orientation of the surgical implants has a direct impact on the postoperative function and long term operability of the implant. Conventional surgical techniques use simple "eyeballing" methods or mechanical tools to position the implant. The "eyeballing" method may be found as being insufficient to provide an accurate alignment of the implant components with the bones where the implant is attached. Studies have shown that sub-optimally positioned orthopedic implants correlate to improper loading, increased implant wear, and even implant failure.

Commercially available computer-assisted surgery systems use tracked tools using optical or magnetic tracking systems. These systems are able to track patient coordinate system accurately and reliably. However, the factors, such as high costs, limited operating range, maintaining a line of sight contact, magnetic interferences, are main issues associated with these technologies.

Inertial sensors have hence been used as tracking technology in computer-assisted surgery. Inertial sensors do not rely on signal transmission and are immune to electromagnetic disturbances during operation. Therefore, inertial sensors are well suited for applications in the OR environment containing a large amount of equipment.

SUMMARY OF THE APPLICATION

It is therefore an aim of the present disclosure to provide a novel method and system to assist in positioning the acetabular cup using inertial sensors.

Therefore, in accordance with the present application, there is provided a method for assisting in positioning the acetabular cup comprising: orienting a cup positioning instrument with a cup thereon in an initial reference orientation relative to an acetabulum of a pelvis with the cup forming a joint with the acetabulum, the cup positioning instrument comprising an inertial sensor unit with pre-planned orientation data for a desired cup orientation based on at least one landmark of the pelvis; rotating the cup positioning instrument to a desired abduction angle as guided by an interface of the cup positioning instrument, based on movements relative to at least one landmark; rotating the cup positioning instrument to a desired anteversion angle as guided by the interface of the cup positioning instrument, based on movements relative to the at least one landmark; and upon reaching the desired cup orientation as indicated by the interface, impacting the cup into the acetabulum.

Still further in accordance with the present disclosure, The method according to claim 1, wherein orienting the cup positioning instrument in an initial reference orientation comprises orienting the cup positioning instrument to a vertical orientation with the patient in lateral decubitus.

Still further in accordance with the present disclosure, orienting the cup positioning instrument in an initial reference orientation comprises pointing a visual guide toward the at least one landmark, and wherein rotating the cup positioning instrument comprises rotating the cup positioning instrument while the visual guide points toward the at least one landmark.

Still further in accordance with the present disclosure, orienting the cup positioning instrument in an initial reference orientation comprises pointing another visual guide on a second landmark.

Still further in accordance with the present disclosure, orienting the cup positioning instrument in an initial reference orientation further comprises orienting the cup positioning instrument to a vertical orientation with the patient in lateral decubitus, and wherein the at least one landmark is a frontal plane of the patient Still further in accordance with the present disclosure, orienting the cup positioning instrument in an initial reference orientation further comprises pointing the visual guide toward the ASIS as the second landmark.

Still further in accordance with the present disclosure, a registration device is positioned to support the inertial sensor unit in a planned manner in the acetabulum of the pelvis to record a pre-operative pelvic coordinate system on the inertial sensor unit, and transferring the inertial sensor unit to the cup positioning instrument prior to orienting the cup positioning instrument.

Still further in accordance with the present disclosure, positioning the registration device in the planned manner comprises inserting a base of the registration device in the acetabulum, and abutting a patient-specific contour matching abutment surface of the registration device against the pelvis.

Still further in accordance with the present disclosure, a registration device is positioned in a planned manner in the acetabulum of the pelvis, a tracker device is secured to the pelvis using the registration device to record a pre-operative pelvic coordinate system on an inertial sensor unit of the tracker device, and transferring pelvic coordinate system to the inertial sensor unit of the cup positioning instrument prior to orienting the cup positioning instrument.

In accordance with another embodiment of the present disclosure, there is provided a cup impactor assembly comprising: a shaft; a cup coupler at a cup end of the shaft adapted to releasably connect a cup in fixed relation for subsequent impacting; a handle at an impacting end of the shaft; a visual guide mounted to at least one of the shaft and the handle, the visual guide producing visual guidance toward at least one anatomical landmark of a pelvis; an inertial sensor unit adapted to produce at least an orientation output related to an orientation of the cup impactor assembly and having a patient-specific file comprising: calibration data based on a planned geometric relation between an initial reference orientation of the cup impactor assembly and the at least one anatomical landmark of the pelvis via the visual guidance of the visual guide, the calibration data for calibrating the inertial sensor unit relative to the pelvis for the inertial sensor unit to produce said orientation output; and a desired acetabular cup orientation data based on preoperative planning.

Still further in accordance with the present disclosure, the visual guide is a light projector.

Still further in accordance with the present disclosure, the light projector projects two light beams angled relative to each other by a patient-specific angle based on a position of landmarks relative to one another, the planned geometric relation including the patient-specific angle.

Still further in accordance with the present disclosure, the initial reference orientation of the cup impactor assembly comprises a vertical orientation of the shaft with the patient in lateral decubitus with the visual guide pointing to two landmarks, the orientation output requiring that one of the two landmarks be pointed during movement to the desired acetabular cup orientation.

In accordance with another embodiment of the present disclosure, there is provided a kit comprising the cup impactor assembly as defined above, further comprising a registration device having a base adapted to be received in the acetabulum, a patient-specific contour matching abutment surface adapted to be abutted against the pelvis in accordance with a planned pelvic coordinate system, the registration device having a coupler adapted to be coupled to the inertial sensor unit to transfer the planned pelvic coordinate system prior to being used with the cup impactor assembly.

DESCRIPTION OF THE EXEMPLARY EMBODIMENTS

Referring to the drawings, there is shown a sequence of steps to assist in positioning the acetabular cup using inertial sensors, to a planned orientation. The proposed method and system and method have minimum modifications on standard surgical techniques and instruments. For instance, instrumentation described hereinafter can be adaptable to surgeons' current practice, in that the instruments used are similar to standard surgical instruments that surgeons typically use in their daily practice. Moreover, surgical techniques using the proposed instrument are similar to the standard surgical techniques.

Pre-Operative Planning

The method of the present disclosure assists in orienting an acetabular cup implant as a function of a pre-operatively planned orientation. It is known that the orientation of the cup implant in the acetabulum has an abduction component and an anteversion component. The abduction (a.k.a., inclination) is the angle between the longitudinal axis (cranial-caudal axis) and the projection of the axis of the cup (i.e., the axis being normal to a rim of the cup) on the frontal plane. The anteversion is the angle between the acetabular axis and the frontal plane. Hence, often times the orientation of the cup is at a 3D angle relative to the standard patient planes (i.e., transverse plane, frontal plane, sagittal plane). Other definitions could be used for the anteversion and abduction, for instance based on anatomical or operative standpoints.

Figure 1:
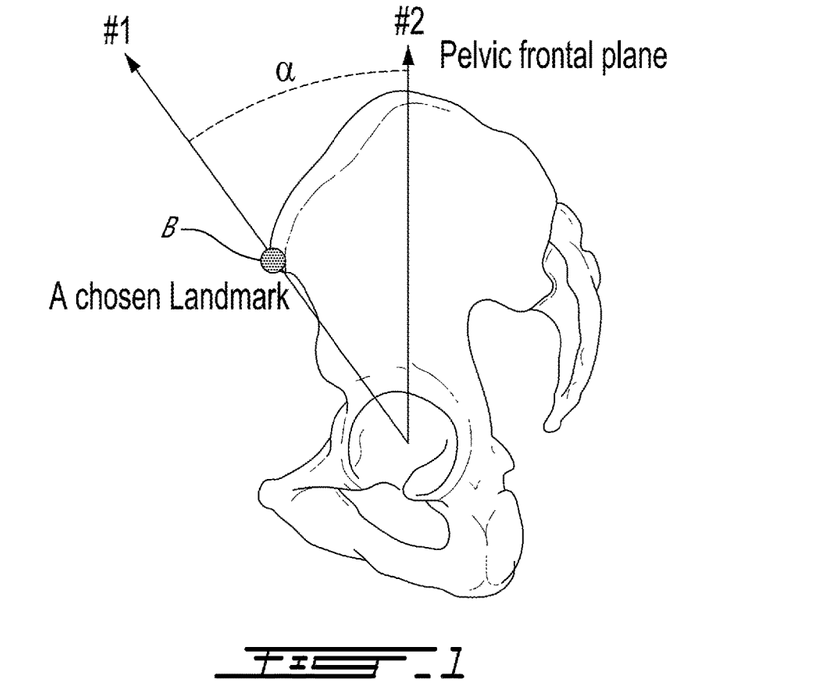
FIG. 1 is a schematic view of a planned reference angle for subsequent acetabular cup positioning navigation.
Figure 2:
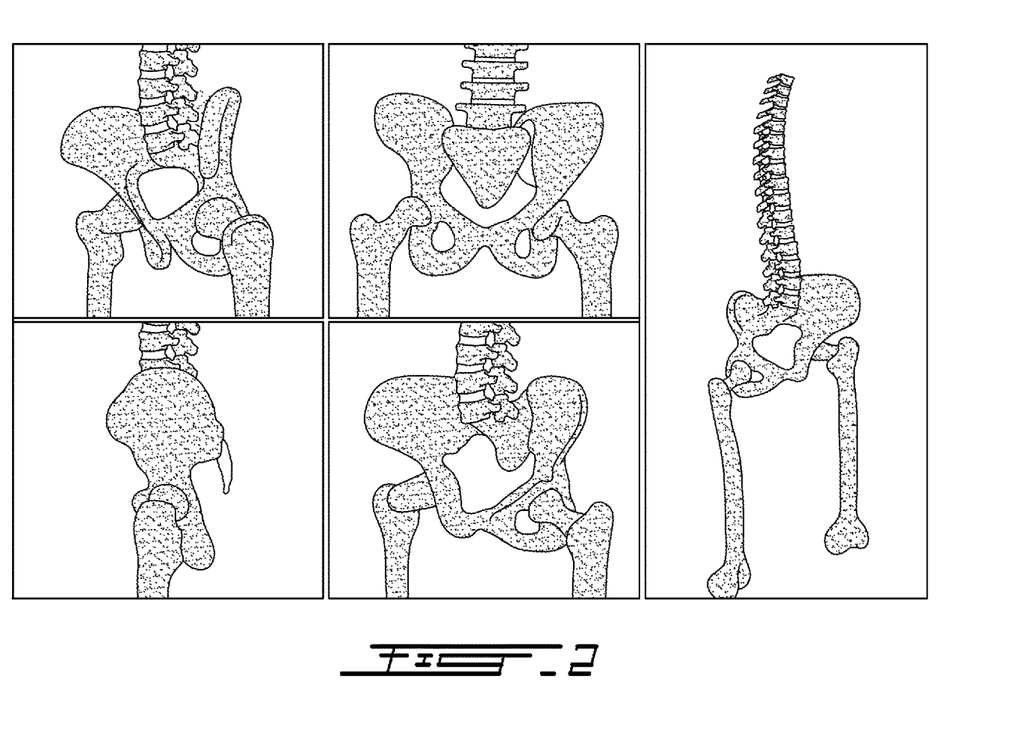
FIG. 2 is schematic view of 3-D models that may be used in the method of the present disclosure.

According to an embodiment, referring to FIG. 1, angle $\alpha$ is measured based on the patient's hip model. As shown in FIG. 2, the hip model may be a 3D hip model being the output from 3D reconstruction software using 2 orthogonal x-ray images, or any appropriate images (e.g., 2D lateral view as shown in FIG. 1, etc) from any appropriate imaging technique. In FIG. 1, angle $\alpha$ is defined by the angle between two lines. A first line connects the acetabulum center A and a chosen landmark B on the pelvis, such as the anterior-superior iliac spine (ASIS) on the operated side. A second line lies in the pelvic frontal plane and passes through the acetabulum center A. Other lines could be used, although the first and second line described are respectively related to a visually distinct landmark (ASIS) and a common reference plane (frontal plane). Other planning operations may be performed, for instance to determine reaming parameters, abduction and anteversion angles, implant dimensions, as well as for femoral planning.

Intra-Operative Steps

Figure 3:
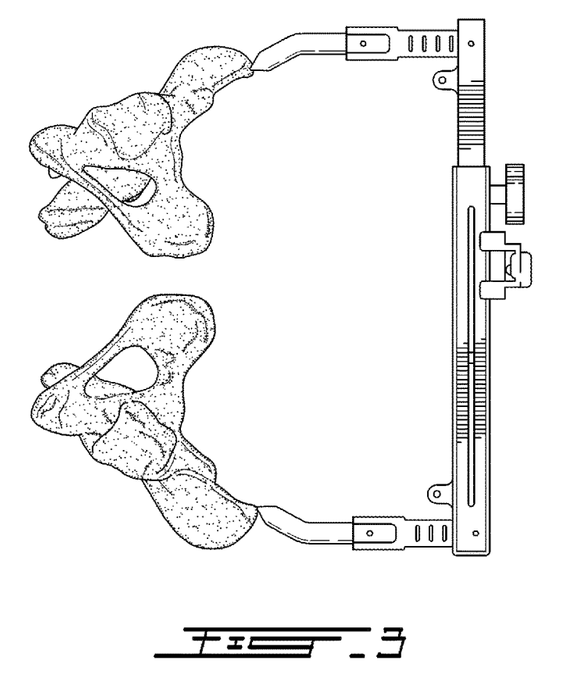
FIG. 3 is an elevation view of a pelvis in lateral decubitus and a pelvic positioning instrument.

According to an embodiment, the patient is physically positioned in a strict lateral decubitus, i.e., one ASIS above the other, such that the axis passing through the ASIS is aligned with gravity. A pelvic positioning instrument such as shown in FIG. 3 and described in U.S. Patent Application Ser. No. 61/677,106, filed on Jul. 30, 2012, may be used to verify that the patient is in strict lateral decubitus. Any appropriate tracking device may be used to indicate the correct hip positioning. Moreover, it may be possible to use manual constraints to position and maintain the patient in strict lateral decubitus.

The femoral head may then be dislocated to expose the acetabulum. Reaming may be performed by the surgeon. The reaming may be guided by the pre-operative planning, for instance with respect to the reamer size, etc. After these steps, it may be required to verify that the hip remains in strict lateral decubitus, with repositioning of the hip being performed as needed.

Figure 4:
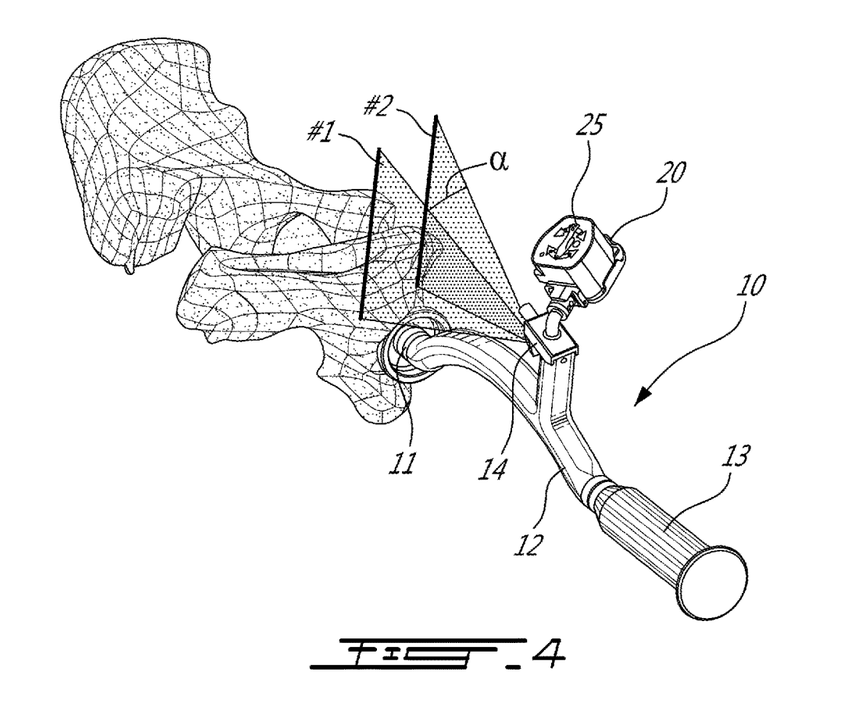
FIG. 4 is a perspective view of a cup positioning instrument relative to a pelvis, as being calibrated for impacting use.

Referring to FIG. 4, a cup positioning instrument 10 at an end of which an acetabular prosthesis cup (implant cup) is positioned, places the implant cup in the acetabulum. The cup positioning instrument 10 is similar in configuration to an impactor, in that it comprises a head 11 to which is mounted the implant cup, and an arm 12 and handle 13 with an impactor end, by which impacts may be transmitted to drive the implant cup in the reamed acetabulum. The head 11 is arranged such that an axis of the arm and handle is normal to a plane in which lies the rim of the implant cup. Stated differently, in an embodiment, the axis of the handle 13 is coincident with the axis of the cup, which cup axis is the reference to orient the cup in the acetabulum.

The instrument 10 further comprises a light projector (e.g., laser projector) as shown at 14 and an inertial sensor unit as shown at 20, both mounted to the arm or handle of the instrument in a known orientation, to track the instrument 10. The light projector 14 is arranged to produce light beams such that the light beams lie in the same plane as the axis of the instrument 10. Alternatively, visual guides such as pointing rods or like visual guides may be used.

Figure 6:
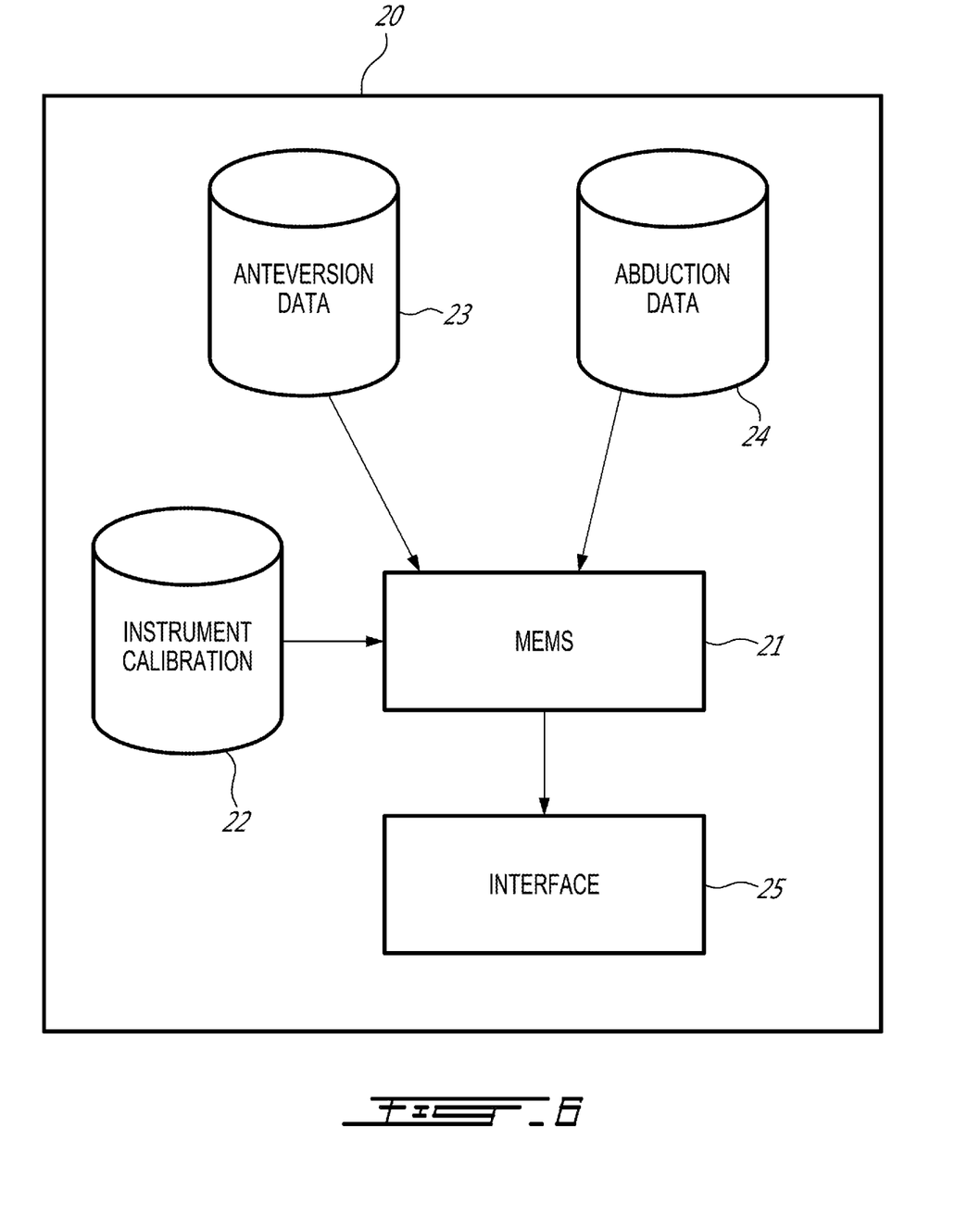
FIG. 6 is a block diagram of an inertial sensor unit of the cup positioning instrument.

The inertial sensor unit 20 is shown in greater detail in FIG. 6 and comprises appropriate micro-electromechanical sensors 21 (e.g., accelerometers, gyroscopes, inclinometers, or the like) and associated electronics and processor chosen to perform the tasks described hereinafter by outputting real-time orientation data related to the movements of the inertial sensor unit 20. The inertial sensor unit 20 is preprogrammed as a function of the pre-operative planning to perform the tasks described hereinafter. It is however known that the inertial sensor unit 20 must be calibrated for its readings to be related to the orientation of the pelvis, and may have a patient-specific file for calibration and navigation. As a starting point, instrument calibration data 22 is for instance provided for the inertial sensor unit 20 to be aligned at initialization with the shaft axis of the instrument 10. The instrument calibration data is based on a planned geometric relation between an initial reference orientation of the instrument 10 and an anatomical landmark(s) of the pelvis via visual guidance of light projector 14 or like visual guidance, the calibration data being used to calibrate the inertial sensor unit 20 relative to the pelvis for the inertial sensor unit 20 to be able to produce the orientation output based on the preoperative planning. The patient-specific file may also include a desired acetabular cup orientation data based on preoperative planning. The desired acetabular cup orientation data may for instance consists of anteversion angle data 23 and/or abduction angle data 24 also programmed into the inertial sensor unit 20, as a function of the pre-operative planning, the anteversion angle data 23 being representative of the anteversion angle at which the operator wants the cup to be, while the abduction angle data 24 is representative of the abduction angle at which the operator wants the cup to be. An interface 25, of any appropriate form, will also be provided as part of the inertial sensor unit 20, directly thereon or remotely therefrom. The interface 25 may be in the form of LEDs signaling a proper/improper orientation, or being a screen giving the numeric angle values.

When maintaining the implant cup in the acetabulum, prior to impacting, the instrument 10 is arranged to be vertical (i.e., an initial reference orientation). According to an embodiment, the inertial sensor unit 20 is used to guide the operator in achieving verticality of the instrument 10. For instance, LEDs may be provided on inertial sensor unit 20 to provide visual indication when appropriate verticality is reached. When the patient is in strict lateral decubitus, the verticality has the shaft axis of the instrument 10 lying in the frontal plane of the patient.

Figure 5:
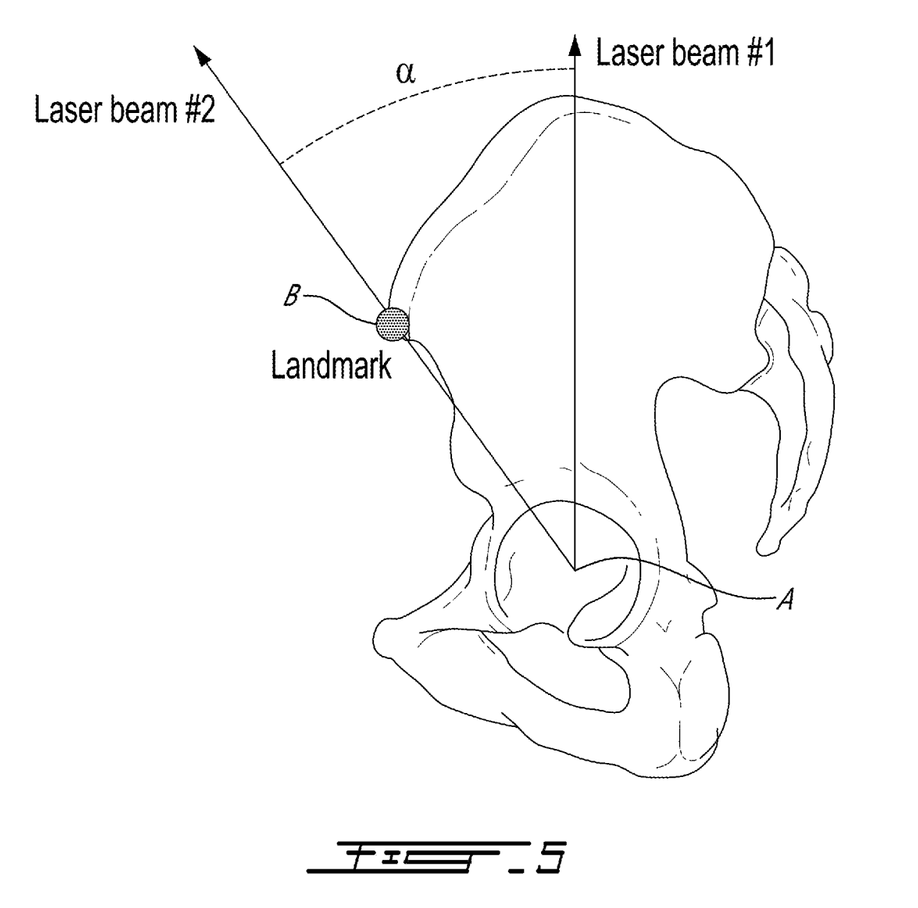
FIG. 5 is a schematic view of the reference angle as during calibration.

Then, as in FIG. 5, the light beams 1 and 2 are aligned with the chosen landmarks, for instance the ASIS A and the frontal plane, with the instrument 10 having its axis passing through the center of rotation of the acetabulum by mating engagement of the cup therein. To do so, the laser beams can be separated from one another by angle α. Light beam #2 is rotated by α° (i.e., the value obtained in pre-operative planning) from light beam #1, as light beam #1 stays as pointing toward the chosen landmark. As a result, laser beam #2 gives the patient frontal plane indication (i.e. local north). In these steps of rotating the light beams, the instrument 10 is kept vertical using the indication provided by the inertial sensor unit 20. By having the light beams #1 and #2 pointing to the landmark B and the frontal plane while the inertial sensor unit 20 is vertical, the inertial sensor unit 20 is calibrated whereby it may be used to calculate the shaft axis orientation relative to the desired implant orientation (e.g., in abduction and anteversion).

The instrument 10 is then rotated within the pelvic frontal plane, i.e., with the light beam #2 remaining in orientation. It is contemplated to draw a continuation of the light beam #2 on the drape or use any like visual marker prior to this rotation, and use such visual marker during the rotation to ensure that the light beam #2 remains aligned with the frontal plane. As the abduction angle was pre-planned, the inertial sensor unit 20 has been calibrated for indication of desired abduction angle. Hence, this abduction-adjusting rotation is guided by the inertial sensor unit 20, for instance by a LED being lit on the inertial sensor unit 20 (e.g. from a $1^{st}$ array of LEDs on the inertial sensor unit 20), which indicates the target abduction angle is achieved, or by way of numerical data being provided to indicate the abduction angle.

The instrument 10 may also be rotated to a target anteversion angle. This is done by rotating the instrument 10 orthogonally relative to the light beam #2, i.e., by ensuring that the laser beam #2 remains relatively fixed during this articulation. Similarly to abduction, this anteversion-adjusting rotation is guided by the inertial sensor unit 20, for instance by a LED being lit on the inertial sensor unit 20 (e.g. from a $2^{nd}$ array of LEDs on the inertial sensor unit 20), which indicates the target anteversion angle is reached, or by way of numerical data being provided to indicate the anteversion angle.

The abduction-adjusting and anteversion-adjusting rotations can be combined as one single movement. The target abduction and anteversion angles can be constantly lit on the inertial sensor unit 20 (e.g., indicated separately on the two arrays of LEDs that are orthogonal to each other), or the two sets of numerical angles may be provided simultaneously. In such an arrangement of arrays, the current cup orientation may be given by two red LEDs which display the real-time orientation. As the instrument 10 approaches the target abduction and anteversion orientations, the red LEDs should converge to the target LEDs (green). The actually position of the target LEDs will be displayed differently, in accordance with pre-operative planning by which the inertial sensor unit is configured with target anteversion and abduction angle. When the inertial sensor unit 20 indicates that the target angles are reached (for instance with the numerical display or light indicator), the implant cup is oriented as planned in anteversion and abduction, and impaction can be performed. As mentioned above, the interface 25 may be a miniature LED screen showing both the target cup orientation and instrument's current orientation in numerical value, which provides visual guidance of the instrument 10 during the cup navigation.

The above is one sequence of steps among others that can be performed in any appropriate order to reach a desired orientation for the implant cup. The sequence of steps may be modified where appropriate. For instance, the anteversion-adjusting rotation may be done prior to the abduction-adjusting rotation.

As alternative to the method described above, another approach is defined below.

Pre-Operative Planning

During planning, several landmarks are chosen on the pelvis or on the spine, e.g. ASIS, landmarks on the acetabular rim, landmarks on the sacrum, or any other identifiable landmarks on the spine, using the images and/or model.

A pelvic coordinate system or a local coordinate system containing the pelvis is built using the known angular and geometrical measurements from the 3D model, using the chosen landmarks. The target cup orientation (with anteversion and abduction angles) may be calculated with respect to this coordinate system. It is considered to use a registration device 30 as in FIGS. 7 and 8.

Intra-Operative Steps

During the intra-operative steps, the landmarks measured/identified in the pre-operative planning with model are identified intraoperatively and the known angular and geometrical measurements acquired in the model will be applied to find the pelvic coordinate system or the coordinate system containing the pelvis.

Figure 7:
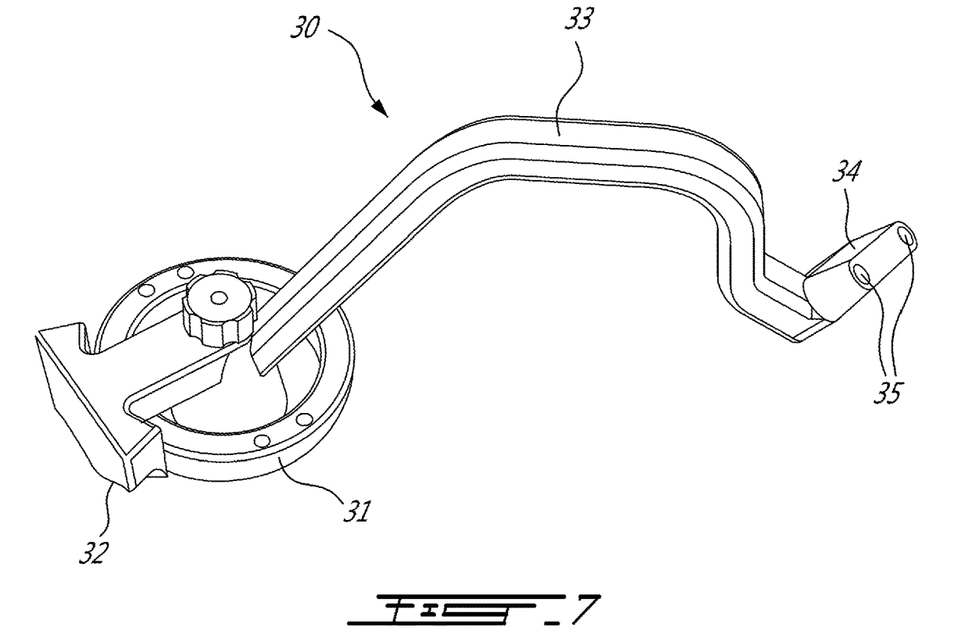
FIG. 7 is a perspective view of a registration device used with the cup positioning instrument of FIG. 4, in accordance with an embodiment of the present disclosure.
Figure 8:
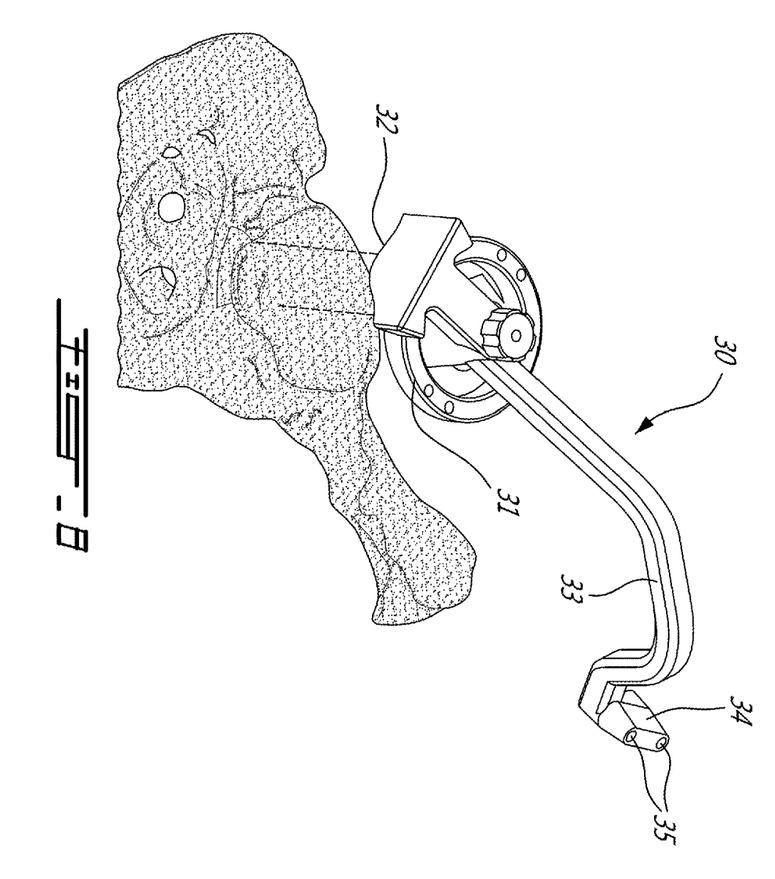
FIG. 8 is a perspective view of the registration device of FIG. 7 relative to a pelvis.

This can be achieved by the registration device 30 shown in FIGS. 7 and 8. The device 30 has a cup-like base 31 that is sized as a function of the reamed acetabulum, so as to be snuggly received therein, in the manner shown in FIG. 8, and is hence placed in the acetabulum during the operation (e.g. after reaming the native acetabulum). The device 30 may also have a patient-specific abutment 32, that has a contact surface fabricated in contour matching to be a replica of a corresponding surface of the pelvis, to ensure a high-precision complementary engagement between the patient-specific abutment 32 and the pelvis (with the cup-like base 31 in the reamed acetabulum. The patient-specific abutment 32 is based on the data obtained pre-operatively, and has a 3D contour matching geometry, whereby the 3D model of pre-planning is used in the fabrication process (e.g., 3D printing, NC machining, etc).

By way of the above-referred configuration, the device 30 identifies several pelvic landmarks simultaneously, whereby it may be used to secure one of the inertial sensor units 20 to the pelvis in such a way that the orientation of the inertial sensor unit 20 is known relative to the pelvic coordinate system. More specifically, knowing the geometrical & angular relation of these landmarks that was established in preoperative planning and used by contact with the base 31 and the patient-specific abutment 32 with the pelvis, the device 30 is in a known orientation relative to the pelvic coordinate system intra-operatively. For this purpose, the registration device 30 has an arm 33 projecting away from the base 31, and having an interface 34. The interface 34 may be a coupler to receive in a known manner one of the inertial sensor units 20 thereon, or may alternatively be provided with a pair of guides 35. In this alternative embodiment, the pair of guides 35 may be used to drive Steinmann pins or equivalent support into the pelvis, to attach one of the inertial sensor units 20 thereto, which inertial sensor unit 20 is part of a tracking device. The geometry of the arm 33 and interface 34 is selected based on the planning data to drive the pins into a desired location of the pelvis, in a desired orientation, such that the pelvic coordinate system may be transferred to an inertial sensor unit 20 that is rigidly attached to the pins or like support.

Depending on the nature of the registration device 30 (i.e., having either a coupler for inertial sensor unit 20 or a pair of guides 35), the subsequent steps are performed.

According to a $1^{st}$ option, the inertial sensor unit 20 directly on the coupler of the registration device 30 is turned on when the registration device 30 is mounted to the pelvis in the manner shown in FIG. 8. The inertial sensor unit 20 is preprogrammed with the pelvic coordinate system which is known from preplanning. Hence, by being turned on at that moment, the inertial sensor unit 20 is calibrated, and may be removed from the registration device 30 and positioned on the instrument 10. A geometric constraint is then applied between the instrument 10 and the pelvic landmarks. The light projector can be used to achieve this constraint. Therefore, the target cup orientation can be transferred from the pelvic coordinate system to the local coordinate system of the instrument 10, and hence taken in consideration by the inertial sensor unit on the instrument 10 to then start navigation for movements toward desired orientation (e.g., anteversion and abduction). This option assumes that the pelvis stays stationary or quasi-stationary after reaming.

According to a $2^{nd}$ option, using the registration device 30 with the guides 35, the registration device 30 is used as a guide to attach the tracking device with inertial sensor unit 20 on the pelvis at the location preoperatively determined (e.g., with the Steinmann pins). This tracking device will keep track of pelvic movement and update the target cup orientation in the local coordinate system of the inertial sensor unit 20 on the instrument 10 placed in the reamed acetabulum. The target cup orientation is programmed into and indicated by the inertial sensor unit 20 attached to the instrument 10, with the constraint that the two inertial sensor units (on the tracker device secured to the Steinmann pins and on the instrument 10) must be linked by a common reference. For example, this common reference can be achieved by laser beams or a mechanical linkage that provide constraint between the two inertial sensor units 20. Therefore, the inertial sensor unit on the instrument 10 gives the target cup orientation without the need for light projectors 14.

Similar approaches may be taken based on other patient positions, for instance in supine decubitus.

The invention claimed is:

1. A cup impactor assembly comprising:
    a shaft;
    a cup coupler at a cup end of the shaft adapted to releasably connect a cup in fixed relation for subsequent impacting;
    a handle at an impacting end of the shaft;
    a light projector mounted to at least one of the shaft and the handle, the light projector producing visual guidance toward at least one anatomical landmark of a pelvis, the light projector projecting at least two light beams angled relative to each other so as to diverge from one another from the light projector;
    an inertial sensor unit configured for producing at least an orientation output related to an orientation of the cup impactor assembly, the inertial sensor unit including a processor and a program executable by the processor and including:
        calibration data based on a planned geometric relation between an initial reference orientation of the cup impactor assembly and the at least one anatomical landmark of the pelvis as aligned with the visual guidance of the light projector, the calibration data for calibrating the inertial sensor unit relative to the pelvis for the inertial sensor unit to produce said orientation output; and
        a desired acetabular cup orientation data based on preoperative planning.

2. The cup impactor assembly according to claim 1, wherein the light projector projects the two light beams angled relative to each other by a patient-specific angle based on a position of landmarks relative to one another, the planned geometric relation including the patient-specific angle.

3. The cup impactor assembly according to claim 1, wherein the initial reference orientation of the cup impactor assembly comprises a vertical orientation of the shaft with the patient in lateral decubitus with the light projector pointing to two landmarks, the orientation output requiring that one of the two landmarks be pointed during movement to the desired acetabular cup orientation.

4. A system comprising the cup impactor assembly according to claim 1, further comprising a registration device having a base adapted to be received in the acetabulum, a patient-specific contour matching abutment surface adapted to be abutted against the pelvis in accordance with a planned pelvic coordinate system, the registration device having a coupler adapted to be coupled to the inertial sensor unit to transfer the planned pelvic coordinate system prior to being used with the cup impactor assembly.

5. A system comprising:
   a cup impactor including a shaft, a cup coupler at a cup end of the shaft adapted to releasably connect a cup in fixed relation for subsequent impacting, a handle at an impacting end of the shaft, a visual guide mounted to at least one of the shaft and the handle, the visual guide producing visual guidance toward at least one anatomical landmark of a pelvis; and
   an inertial sensor unit configured for producing at least an orientation output related to an orientation of the cup impactor, the inertial sensor unit including a processor and a program executable by the processor and including:
      calibration data based on a planned geometric relation between an initial reference orientation of the cup impactor assembly and the at least one anatomical landmark of the pelvis as aligned with the visual guidance of the visual guide, the calibration data for calibrating the inertial sensor unit relative to the pelvis for the inertial sensor unit to produce said orientation output, and
      a desired acetabular cup orientation data based on preoperative planning.

6. The system according to claim 5, wherein the visual guide is a light projector.

7. The system according to claim 6, wherein the light projector projects two light beams angled relative to each other by a patient-specific angle based on a position of landmarks relative to one another, the planned geometric relation including the patient-specific angle.

8. The system according to claim 6, wherein the initial reference orientation of the cup impactor assembly comprises a vertical orientation of the shaft with the patient in lateral decubitus with the visual guide pointing to two landmarks, the orientation output requiring that one of the two landmarks be pointed during movement to the desired acetabular cup orientation.

9. The system according to claim 6, further comprising a registration device having a base adapted to be received in the acetabulum, a patient-specific contour matching abutment surface adapted to be abutted against the pelvis in accordance with a planned pelvic coordinate system, the registration device having a coupler adapted to be coupled to the inertial sensor unit to transfer the planned pelvic coordinate system prior to being used with the cup impactor assembly.

* * * * *